United States Patent [19]
Takahashi et al.

[11] Patent Number: 5,692,899
[45] Date of Patent: Dec. 2, 1997

[54] WIRE FOR ORTHODONTIC TREATMENT AND ITS MANUFACTURING METHOD

[75] Inventors: Osamu Takahashi, Chiba; Hitoshi Hamanaka, 2-6, Maruyama 1-chome, Nakano-ku, Tokyo; Takayuki Yoneyama, 16-3, Kataseyama 3-chome, Fujisawa-shi, Kanagawa, all of Japan

[73] Assignees: Seiko Instruments Inc.; Hitoshi Hamanaka; Takayuki Yoneyama, all of, Japan

[21] Appl. No.: 495,755

[22] Filed: Jun. 26, 1995

[30] Foreign Application Priority Data

Jun. 24, 1994 [JP] Japan ................... 6-143578

[51] Int. Cl.⁶ .................................. A61C 3/00
[52] U.S. Cl. .................................. 433/20
[58] Field of Search .................................. 433/20

[56] References Cited

U.S. PATENT DOCUMENTS

| | | |
|---|---|---|
| 4,037,324 | 7/1977 | Andreasen ............... 433/24 |
| 4,197,643 | 4/1980 | Burstone et al. ............... 433/20 |
| 4,490,112 | 12/1984 | Tanaka et al. ............... 433/20 |
| 4,818,226 | 4/1989 | Berendt et al. ............... 433/20 |
| 5,018,969 | 5/1991 | Andreiko et al. ............... 433/20 |

*Primary Examiner*—Nicholas D. Lucchesi
*Attorney, Agent, or Firm*—Adams & Wilks

[57] ABSTRACT

A wire for orthodontic treatment comprises an orthodontic wire made of a Co—Ni based alloy. The orthodontic wire is manufactured by subjecting it to a final cold reduction of 60 to 90%. The wire is worked into a linear shape by, for example, a mechanical straightening method, in order to correct waviness of the wire resulting from the final cold reduction. The wire is then aged at a temperature of 500° through 600° C. to provide an orthodontic wire which has a high mechanical strength, an excellent corrosion resistance and a superior toughness.

26 Claims, 1 Drawing Sheet

WIRE FOR ORTHODONTIC TREATMENT AND ITS MANUFACTURING METHOD

BACKGROUND OF THE INVENTION

The present invention relates to a wire for orthodontic treatment which is used to control the final slight movement of teeth, and its manufacturing method.

Several types of orthodontic wires are used in orthodontic treatment and they are selected according to clinical purpose. Super-elastic Ni—Ti alloy wires are used for the first dynamic stage and other alloy wires having a high mechanical strength (especially bending strength) are used for the finishing stage to control the final slight movement of teeth. Conventionally, heat-treated high carbon stainless steel wires having a wire diameter of approximately 0.016 in. (0.4 mm) have been used for the finishing stage to control the final slight movement of teeth.

Although the above-mentioned high carbon stainless steel wire has a high bending strength, it has the follow problems:

(1) It is easily rested.

(2) It breaks easily during bending.

(3) The surface thereof is roughened into a rugged shape by an oxide film caused by a heat treatment.

(4) The wire is provided with curls and is difficult to be formed in conformity with a shape of dentition of a patient.

SUMMARY OF THE INVENTION

To solve the above problems, a Co—Ni base alloy is used for the material of the wire in the present invention which has a high mechanical strength, an excellent corrosion resistance and a higher toughness. The Co—Ni base alloy has been disclosed, for example, in Japanese Patent No. 1374564. The composition of the alloy in Japanese patent No. 1374564 is 20 through 40% of Cr+Mo, 20 through 50% of Ni, 25 through 45% of Co, 0.1 through 5% of Mn, Ti, Al and Fe, 0.1 through 3% of Nb and 0.01 through 1% of one or more than two of rare earth elements selected from the group consisting of Ce, Y and Mischmetall. The wire made of the above-mentioned alloy is drawn by a final cold reduction of 60 through 90%. The cold reduction is 60% or more since a necessary mechanical strength is not provided to the wire if the cold reduction is lower than 60%. The cold reduction is 90% or less since the toughness of the wire is lowered if the cold reduction is more than 90%. After drawing, the wire is straightened into a linear shape by a mechanical method to correct a waviness of wire (curl) caused in drawing and is cut in a length easy to handle. Thereafter, an aging treatment is performed in a furnace having a vacuum or nonoxidizing atmosphere for 1 to 2 hours at a temperature of 500° through 600° C. By this method, a wire for orthodontic treatment having a high mechanical strength and which is difficult to break during bending owing to its excellent toughness, having an excellent corrosion resistance and having a lustrous and smooth surface can be provided.

A wire may be supplied to a dentist which is aged previously by the above-mentioned method and the dentist may bend the wire in conformity with the shape of dentition of a patient, and also the wire may be supplied without performing the aging treatment and the dentist may age the wire by heating it through direct conduction of electricity therethrough after bending since this alloy has an electric resistivity as large as 105 μω –cm. The alloy is provided with a very excellent corrosion resistance and, therefore, the surface is not roughened into a rugged shape since only an extremely thin oxide film is produced even if it is heated by the direct conduction of electricity in the atmosphere.

A wire for orthodontic treatment having a high mechanical strength (bending strength), which does not rust easily and is difficult to break during bending, having a smooth surface and which is easy to form in conformity with a shape of dentition of a patient since it has no curls can be provided by the above-mentioned construction.

DETAILED DESCRIPTION OF THE PREFERRED EMBODIMENT

Details of the present invention are provided below according to a preferred embodiment with reference to FIGS. 1–3 as follows.

An alloy consisting essentially of 20.5% of Cr, 8.9% of Mo, 31.3% of Ni, 36.4% of Co, 0.4% of Mn, 0.6% of Ti, 0.1% of Al, 0.7% of Fe, 1.1% of Nb and 0.01% of Mischmetall was used to make a wire and a drawing of the wire was performed by a final cold reduction of 80% at room temperature using diamond dies. The diameter of the wire was 0.016 in. (0.40 mm). After drawing the wire was straightened into a linear shape by a mechanical method and was cut to a length of 300 mm.

Figure 1:
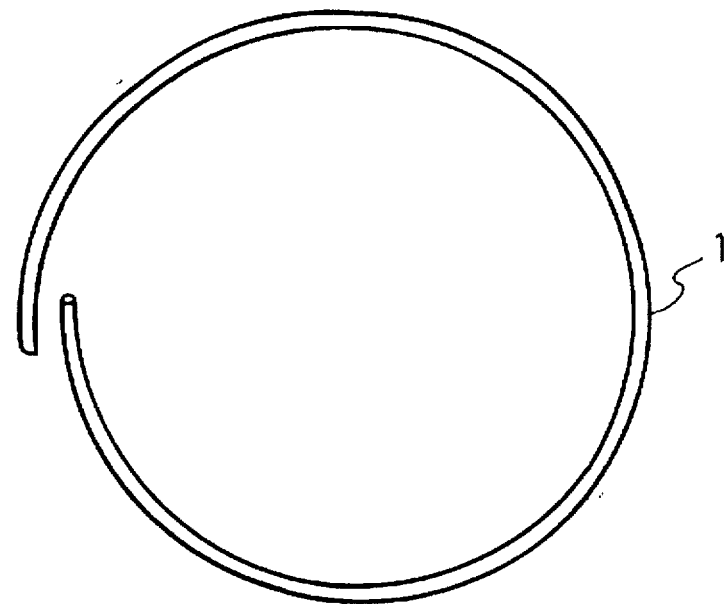
FIG. 1 shows a wire for orthodontic treatment according to the present invention after drawing and having a curl.

FIG. 1 shows the wire 1 after drawing and having a curl.

Figure 2:
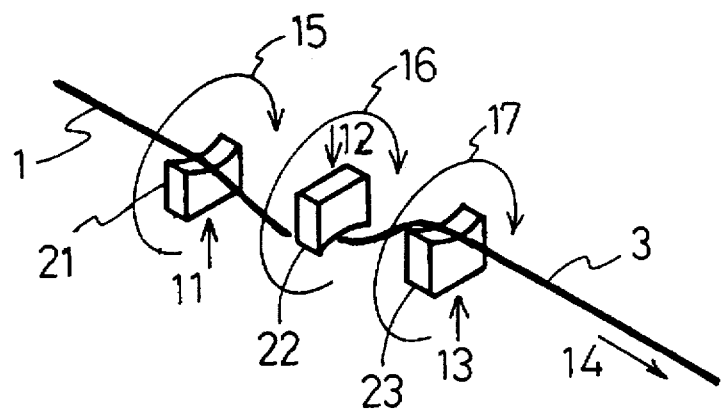
FIG. 2 shows a mechanical method of straightening the wire shown in FIG. 1.

FIG. 2 shows a mechanical method used to straighten the wire. Numeral 3 denotes the wire after correcting (straightened), 11, 12 and 13 are directions of force applied added on each chip 21, 22 and 23 respectively to straighten the wire 1, arrows 15, 16, 17 show rotation directions of each chip, and arrow 14 shows the direction in which the wire is drawn.

Figure 3:
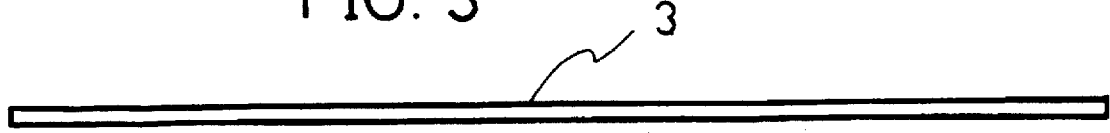
FIG. 3 shows the wire shown in FIGS. 1 and 2 after straightening.

FIG. 3 shows the wire 3 after it has been straightened and cut.

With regard to the linearity, a maximum deviation from a straight line with a wire length of 300 mm was 1 mm or less. The wire manufactured as mentioned above and a wire further aged thereafter in a vacuum atmosphere furnace for 2 hours at 550° C. were prepared respectively and a bending test, a folding test, a corrosion test and measurement of surface roughness were performed thereon. Table 1 shows the maximum bending strength in case where the bending test was performed in which the wire was cut in length of 25 mm and bent to a maximum deflection of 3 mm in a three points bending test.

The maximum bending strength (σ max) is defined as $$\sigma_{max} = \frac{8WL}{\pi d^3}$$

where, W is the maximum load, L is the distance between two supporting points, and d is the diameter of the wire.

It is known that the invented wire has a maximum bending strength approximately equivalent to that of a high carbon stainless steel wire after it has been subjected to an aging treatment.

TABLE 1

| Material of wire | Maximum bending strength (MPa) |
| --- | --- |
| Invented wire (before aging) | 3470 |
| Invented wire (after aging) | 4449 |
| High carbon stainless steel wire | 4488 |

Next, the wire was repeatedly folded by an angle of 90° by using pliers having a corner roundness of 0.1 mmR and the number of foldings resulting in breakage of the wire was investigated. The number of foldings resulting in breakage was 6 for the invented wire before aging, 4 for the invented wire after aging and 3 for a high carbon stainless steel wire.

Next, a corrosion test in which the wire was dipped in an aqueous solution of 10% hydrochloric acid for 7 hours at a solution temperature of 60° C. and in an aqueous solution of 10% sodium chloride for 168 hours was conducted to investigate the corrosion resistance. Table 2 shows amounts of reduction by corrosion (mg/cm$^2$·Hr) per unit area and unit time of the wire at that time and the state of rust formation. It is known that the invented wire has a far more excellent corrosion resistance than a high carbon stainless steel wire.

In the above-mentioned embodiment, a wire having a round cross-sectional shape was used but the shape of the wire is not limited to a round shape. For example, a square cross-sectional shape was used in another embodiment which showed very excellent results as in the above-mentioned embodiment.

TABLE 2

| | (Solution temperature 60° C.) Corrosion conditions | |
| --- | --- | --- |
| Material of wire | Dip in 10% hydrochloric acid aqueous solution for 7 hours (mg/cm$^2$ · hr) | Dip in 10% sodium chloride aqueous solution for 168 hours |
| Invented wire (before aging) | 0.188 | No change |
| Invented wire (after aging) | 0.152 | No change |
| High carbon stainless steel wire | 12.432 | Rust formation on surface |

Next, Table 3 shows the surface roughness of the wire. It is known that the surface roughnesses Rmax of the invented wires before aging as well as after aging are small or the surface is smooth compared with those of a high carbon stainless steel wire.

TABLE 3

| Material of wire | Surface roughness Rmax (μm) |
| --- | --- |
| Invented wire (before aging) | 0.27 |
| Invented wire (after aging) | 0.37 |
| High carbon stainless steel wire | 1.09 |

As explained above, the wire of the present invention has an effect wherein its bending strength is very large, it has a high degree of toughness, is difficult to break during bending, is difficult to rust because of its excellent corrosion resistance, is provided with a lustrous and smooth surface and is easy to form since there is no waviness of wire which is the most suitable for a fixing wire for orthdontic treatment used to control the final slight movement of teeth.

What is claimed is:

1. A wire for orthodontic treatment comprising: an orthodontic wire made of a Co—Ni based alloy.

2. A wire for orthodontic treatment according to claim 1; wherein the Co—Ni based alloy comprises 31.3% Ni and 36.4% Co.

3. A wire for orthodontic treatment, comprising: a wire made of a Co—Ni—Cr—Mo alloy consisting essentially of 20 through 40% Cr+Mo, 20 through 50% Ni, 25 through 45% Co, 0.1 through 5% Mn, Ti, Al and Fe, 0.1 through 3% Nb, and 0.01 through 1% of at least one rare earth element selected from the group consisting of Ce, Y and Mischmetall.

4. A wire for orthodontic treatment according to claim 3; wherein the wire is drawn by cold working to a final reduction of 60 through 90%.

5. A wire for orthodontic treatment according to claim 4; wherein the wire is aged at a temperature of 500° through 600° C.

6. A method for manufacturing a wire for orthodontic treatment, comprising the steps of:
providing a wire made of a Co—Ni based alloy; and
subjecting the wire to a final cold reduction.

7. A method for manufacturing a wire for orthodontic treatment according to claim 6; wherein the providing step comprises providing a Co—Ni based alloy comprising 20 to 50% Ni and 25 to 40% Co.

8. A method for manufacturing a wire for orthodontic treatment according to claim 6; wherein the providing step comprises providing a Co—Ni based alloy comprising 31.3% Ni and 36.4% Co.

9. A method for manufacturing a wire for orthodontic treatment, comprising the steps of:
providing a wire made of a Co—Ni—Cr—Mo alloy consisting essentially of 20 through 40% Cr+Mo, 20 through 50% Ni, 25 through 45% Co, 0.1 through 5% Mn, Ti, Al and Fe, 0.1 through 3% Nb, 0.01 through 1% of at least one rare earth element selected from the group consisting of Ce, Y and Mischmetall; and
subjecting the wire to a final cold reduction of 60 through 90%.

10. A method for manufacturing a wire for orthodontic treatment according to claim 9; including working the wire into a linear shape by mechanical straightening.

11. A method for manufacturing a wire for orthodontic treatment according to claim 9 or claim 10; wherein the wire is aged at a temperature of 500° through 600° C.

12. A wire for orthodontic treatment according to claim 1; wherein the Co—Ni based alloy comprises 20 to 50% Ni and 25 to 45% Co.

13. A wire for orthodontic treatment according to claim 12; wherein the wire is worked into a linear shape by mechanical straightening.

14. A wire for orthodontic treatment according to claim 13; wherein the wire is aged at a temperature of 500° through 600° C.

15. A wire for orthodontic treatment comprising: a cold-drawn wire composed of a Co—Ni based alloy.

16. A wire for orthodontic treatment according to claim 15; wherein the wire has a final cold-drawn reduction of 60 to 90%.

17. A wire for orthodontic treatment according to claim 15; wherein the wire is aged at a temperature of 500° to 600° C.

18. A wire for orthodontic treatment according to claim 15; wherein the wire has a mechanically straightened linear shape.

19. A wire for orthodontic treatment according to claim 15; wherein the Co—Ni based alloy comprises 20 to 50% Ni and 25 to 45% Co.

20. A wire for orthodontic treatment according to claim 15; wherein the Co—Ni based alloy comprises 31.3% Ni and 36.4% Co.

21. A method of manufacturing an orthodontic wire comprising: providing a wire made of a Co—Ni based alloy; cold working the wire to a final cold reduction; working the cold-worked wire into a linear shape; and aging the wire at a preselected temperature.

22. A method according to claim 21; wherein the wire is subjected to a final cold reduction of 60 to 90%.

23. A method according to claim 21; wherein the wire is aged at a temperature in the range of about 500° to 600° C.

24. A method according to claim 21; wherein the wire is worked into a linear shape by mechanical straightening.

25. A method according to claim 21; wherein the Co—Ni based alloy comprises 20 to 50% Ni and 25 to 45% Co.

26. A method according to claim 21; wherein the Co—Ni based alloy comprises 31.3% Ni and 36.4% Co.

* * * * *